(12) United States Patent
Kloeffel et al.

(10) Patent No.: US 10,507,273 B2
(45) Date of Patent: Dec. 17, 2019

(54) METHOD OF FILLING A CONTAINER

(71) Applicant: FRESENIUS MEDICAL CARE DEUTSCHLAND GMBH, Bad Homburg (DE)

(72) Inventors: Peter Kloeffel, Nuedlingen (DE); Olaf Nicholas, Kitzingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 116 days.

(21) Appl. No.: 15/309,625

(22) PCT Filed: May 7, 2015

(86) PCT No.: PCT/EP2015/000929
§ 371 (c)(1),
(2) Date: Nov. 8, 2016

(87) PCT Pub. No.: WO2015/169445
PCT Pub. Date: Nov. 12, 2015

(65) Prior Publication Data
US 2017/0182233 A1 Jun. 29, 2017

(30) Foreign Application Priority Data
May 8, 2014 (DE) .................. 10 2014 006 821

(51) Int. Cl.
*A61M 1/14* (2006.01)
*A61M 1/16* (2006.01)
*B01D 61/30* (2006.01)

(52) U.S. Cl.
CPC .............. *A61M 1/14* (2013.01); *A61M 1/167* (2014.02); *A61M 1/1635* (2014.02);
(Continued)

(58) Field of Classification Search
CPC ...... A61M 1/14; A61M 1/342; A61M 1/3424; A61M 1/3441; A61M 1/3462;
(Continued)

(56) References Cited

U.S. PATENT DOCUMENTS

| 4,431,425 A | 2/1984 | Thompson et al. |
| 2003/0136181 A1* | 7/2003 | Balschat ................. A61M 1/16 73/40.5 R |
| 2013/0004593 A1* | 1/2013 | Kloeffel ................... A61J 1/10 424/678 |

FOREIGN PATENT DOCUMENTS

| DE | 2634238 | 2/1978 |
| DE | 19728280 | 5/1998 |

(Continued)

*Primary Examiner* — Pranav N Patel
(74) *Attorney, Agent, or Firm* — Jacobson Holman, PLLC.

(57) ABSTRACT

A method of filling a container, preferably containing at least one concentrate, with the concentrate being formed such that it forms at least one liquid concentrate or a part of a liquid concentrate on its solution in or its mixing with a liquid, preferably water, the liquid concentrate or the part of the liquid concentrate being suitable for preparing at least one dialysis solution, includes filling the container via a balance chamber system of a dialyzer. The balance chamber system has chambers from which the liquid is conveyed into the container in the form of repeating cycles. The pressure of the liquid being conveyed is measured during a cycle of the filling phase of the container, and an alarm signal is emitted and/or the filling of the container is stopped if a measured maximum pressure in a cycle does not reach or does not exceed a limit value.

19 Claims, 3 Drawing Sheets

(52) U.S. Cl.
CPC ........ *A61M 1/1656* (2013.01); *A61M 1/1666* (2014.02); *A61M 1/1668* (2014.02); *A61M 2205/15* (2013.01); *A61M 2205/18* (2013.01); *A61M 2205/3331* (2013.01); *B01D 61/30* (2013.01)

(58) Field of Classification Search
CPC .............. A61M 1/3437; A61M 1/3444; A61M 1/3448; A61M 1/3465; A61M 1/1635; A61M 1/1641; A61M 1/1639; A61M 1/1656; A61M 1/1666; A61M 1/1668; A61M 1/167; A61M 2205/15; A61M 2205/18; A61M 2205/3331; B01D 2313/105; B01D 2313/243; B01D 61/145; B01D 61/18; B01D 61/30; C02F 1/444
See application file for complete search history.

(56) References Cited

FOREIGN PATENT DOCUMENTS

| | | |
|---|---|---|
| DE | 19728800 | 2/1999 |
| DE | 10100146 | 7/2002 |
| DE | 10201109 | 1/2003 |
| DE | 102011106248 | 1/2013 |
| EP | 0306241 | 3/1989 |
| EP | 1393761 | 3/2004 |

\* cited by examiner

METHOD OF FILLING A CONTAINER

BACKGROUND OF THE INVENTION

1. Field of the Invention

The present invention relates to a method of filling a container, preferably containing at least one concentrate, with the concentrate being formed such that it forms at least one liquid concentrate or a part of a liquid concentrate on its solution in or its dilution with a liquid, preferably water, said liquid concentrate or part of a liquid concentrate being suitable for preparing at least one dialysis solution, and with the filling of the container taking place by means of the balance chamber system of a dialyzer which has chambers from which the liquid is conveyed into the container in the form of repeating cycles.

2. Description of Related Art

It is known from the prior art to prepare a dialysis solution with the aid of dry concentrates. These dry concentrates contain different salts, for example, which are brought into solution by water. The concentrated solution prepared in this manner is used to prepare a dialysis solution, optionally with further concentrates and water which is ready to use and which is then used within the framework of a dialysis process.

To introduce water into the container containing the dry concentrate, a pump or also the balance chamber system of the dialyzer, can be used, for example. Such a procedure as well as a container containing dry concentrate is known, for example, from DE 10 2011 106 248 A1. A balance chamber system serves the control of the volume supplied to the dialysis machine and led off from the dialysis machine during the carrying out of a dialysis treatment.

The balance chamber system typically comprises two rigid chambers of a fixed volume which are each separated by a movable separation membrane into a compartment for fresh dialysis solution (also called "fresh water compartment" in the following) which is conducted toward the dialysis machine during the treatment and into a compartment for consumed dialysis solution (also called "used water compartment") which flows from the dialysis machine into the chamber during the treatment. Liquid, namely fresh dialysis solution from a source for the dialysis solution, is conveyed from both chambers into the dialysis machine and consumed dialysis solution is conveyed from the dialysis machine into the waste during the treatment.

Due to the movement of the separation membrane in the chamber and the actuation of valves which are arranged upstream and downstream of the chambers, the volume conveyed away from the dialysis machine is identical to the volume conveyed toward the dialysis machine.

If such a balancing system of the dialyzer is used for filling a concentrate container, no consumed dialysis solution is introduced from the dialysis solution into the balancing system.

On the filling of the container by means of the chambers of the balance chamber system, care must be taken that the total filling volume corresponds to the specifications so that it is ensured that the desired filling quantity is achieved or the dry concentrate is actually dissolved or the correct mixing ratio is maintained and thus the desired concentrations of the dissolved substances in the prepared liquid concentrate are achieved.

If the total filling volume, i.e. the conveyed liquid volume conveyed into the container in total is determined from the number of filling cycles and the conveyed filling volume per cycle, it must thus be ensured that the filling volume conveyed per cycle corresponds to the specifications or is known. If a leak or leakage occurs, for example in a valve which closes a chamber of the balance chamber system, this would have the consequence that the filling volume supplied to the container per cycle and thus the total filling volume does not correspond to the desired value, which is naturally unwanted. For the dissolving of the granulate located in the container is an important aspect in concentrate preparation. Measurements have shown that the granulate of typical containers completely dissolves from a filling volume of 3.6 l. To ensure this filling volume, limit values, i.e. tolerances, can be fixed at a level of 50 μl/switchover, for example, which may not be exceeded.

If this limit value of the filling volume is nevertheless exceeded, e.g. due to a leakage, this would under certain circumstances have the consequence of an insufficient dissolving of the dry concentrate and thus concentrations of the substances in the liquid concentrate which lie outside the comparatively narrow specification limits. The same applies accordingly on the use of liquid concentrates. It must also be ensured with these that the solution obtained by mixing has the desired concentrations.

An apparatus for leak recognition of the movable separation wall of a membrane apparatus for conveying an infusion solution having an optical sensor is described in U.S. Pat. No. 4,431,425. DE 197 28 280 C1 discloses an apparatus for conveying liquids for a medical treatment apparatus in which the number of pressures pulses over time is monitored.

The pressure holding tests of the valves of the balance chamber system and of the connected line system carried out as standard are not sensitive enough so that a sensitively reacting monitoring process for the leak tightness of the system is necessary.

SUMMARY OF THE INVENTION

It is thus the underlying object of the present invention to provide a method by means of which it can be reliably recognized whether a leak of the balance chamber system or of the line system connected thereto is present by which the conveying volume conveyed in the container is reduced.

This object is achieved by a method having the features of claim 1. Provision is made in accordance with this that the time development of the pressure is measured during a cycle of the filling phase of the container and that an alarm signal is emitted and/or the filling process of the container is stopped when the measured maximum pressure in a cycle does not reach or does not exceed a limit value. The container which can be empty before its filling in accordance with the method in accordance with the invention or can contain concentrate will simply be called a "container" or a "dry concentrate container" in the following.

It is pointed out at this point that the container content does not necessarily have to be a dry concentrate although the invention has particular relevance for the dissolving of dry concentrates. The invention is thus not restricted to the dissolving of dry concentrates although they represent a preferred embodiment of the invention. The container content can also be a liquid concentrate which is diluted by the addition of liquid or can also be a mixture of a liquid concentrate and a dry concentrate.

The filling of an empty container and thus also of a container not containing any concentrate is also covered by the invention.

The term "cycle" is to be understood as a length of time which comprises the emptying of a compartment of a chamber. Such a cycle preferably comprises the opening of a valve through which the liquid runs out of the compartment of the chamber, the emptying of this compartment and the subsequent closing of this valve. In this respect, the valve is closed via which the compartment is filled with fresh liquid. The reverse procedure takes place in a compartment of the other chamber of the balance chamber system during this cycle. The valve through which the liquid runs into the compartment is opened there and the compartment is filled with liquid, while the valve through which the liquid runs out of the compartment is closed.

The cycle is ended when a compartment of a chamber was emptied and a compartment of the other chamber was filled. A new cycle which comprising the emptying of the filled compartment and the filling of the empty compartment begins by a switchover of the valves.

An example for the operation of the balance chamber system taking place in cycles can be found in DE 26 34 238 A1 to which reference is made in this respect.

It is thus the underlying idea of the present invention to carry out a leak tightness determination via the level of the pressure or via the magnitude of the pressure pulses and not via their number. In the expulsion phase of the filling volume from the chamber or from its compartment, the pressure first increases and then drops again so that a pressure pulse arises. On a reaching or falling below of a lower limit value, a switchover or the introduction of a new cycle for filling the container can take place.

The pressure measurement can take place, for example, such that the pressure is measured at which the liquid is which moves from the chamber to the container. The pressure measurement can take place at or in the chamber and/or at or in the line between the chamber and the container and/or at or in the container.

If the pressure measured during such a pressure pulse or other pressure development does not reach or exceed an upper limit value, the conclusion is drawn that a leak must be present. This can result in the emitting of a corresponding signal and/or in the aborting of the filling process of the container. It can be recognized by such a procedure whether the container, which is preferably designed as a bag, is charged with the correct filling volume or with an incorrect filling volume due to the leak. A monitoring of a deviation of the actually conveyed filling volume from the desired filling volume in a magnitude of 50 µl/cycle can be recognized by the method in accordance with the invention.

The balance chamber system of the dialyzer preferably has at least two chambers and an oscillating volume between the two chambers is moved to and fro for the purpose of conveying the liquid into the container. This oscillating volume defines the conveying volume for the dry concentrate container conveyed per balance chamber switchover. The total conveying volume supplied to the container can be determined via the total number of switchovers. The oscillating volume is preferably located in the part of the chambers which is acted on by consumed dialysis solution in treatment operation, i.e. in the used water compartments. The conveying of the liquid into the container preferably takes place by means of the chambers which convey the fresh dialysis solution to the dialysis machine in treatment operation, i.e. by means of the fresh water compartments.

If the balance chamber system comprises two chambers, the oscillation volume is defined by the volume of two compartments of the chambers of the balance chamber system, preferably by the volume of the two used water compartments of the chambers as well as by the lines, including the valves located therein, connecting these two compartments to one another.

The method in accordance with the invention preferably takes place before a dialysis treatment. However, the case is also covered by the invention that the method in accordance with the invention takes place during a dialysis treatment; however, in this case, the container filled by the method in accordance with the invention is not used for the ongoing dialysis treatment. Its use for a dialysis treatment only starts when the method in accordance with the invention for filling a container is ended and a new treatment is taking place.

The oscillating volume preferably corresponds to the volume of a total chamber of the balance chamber system.

If a leak occurs in the system, this can result in a change in the oscillating volume and thus also in a change in the filling volume conveyed per cycle. This leak can be determined by means of the method in accordance with the invention.

Provision is preferably made that the limit value depends on the maximum pressure which was measured in at least one of the preceding cycles. If, for example, a maximum pressure of 400 hPa is measured in one of the preceding cycles for filling the container, provision can be made to determine the limit value for the following cycle or cycles in dependence on this value.

The limit value can be predefined for the first cycle since no preceding cycles exist with reference to which a limit value determination could take place.

It is conceivable that the limit value lies below the highest maximum pressure measured in the preceding cycle by a specific percentage or by a specific absolute value. The limit value can thus, for example, lie beneath the measured maximum value by 10%. The limit value thus amounts to 360 hPa with respect to the given example of a maximum pressure of 400 hPa. The determination of the limit value by deduction of a fixed amount, e.g. 50 hPa, from the maximum pressure is also conceivable.

These values and the values named in the following are only examples which do not restrict the invention.

Provision is preferably made that the maximum pressure is the highest pressure which was measured in all of the preceding cycles. If the maximum pressure values in the preceding cycles lie in a range, for example, between 390 hPa and 400 hPa, the largest value is used as the basis for the determination of the limit value; thus in this case 400 hPa.

Provision is preferably made that the limit value is not lowered in the course of the filling procedure. This means that, with respect to the aforesaid example, the limit value of 360 hPa remains even if maximum pressure values below 400 hPa should result in other, later cycles. In this embodiment, the limit value is thus not oriented on the last-measured maximum pressure, but rather on the largest pressure value which was measured in one of the preceding cycles.

The pressure measurement can, for example, be measured in the line system between the chamber and the container or in a line connected thereto. A pressure measurement at or in the balance chamber or at or in the container itself is also conceivable. Even if the container is in communication with the atmosphere, a characteristic pressure pulse or other pressure development which can be measured results by the flow resistance of the hose system between the balance chamber system and the container.

Provision is preferably made that the pressure first increases on an emptying of a compartment of a chamber and then drops and that an alarm signal is output and/or the filling process of the container is stopped when a lower limit value for the pressure has not reached or has fallen below within a specific time window since the cycle start. It is thus conceivable, for example, that the timeout, i.e. the maximum permitted length of time up to the reaching of the lower limit value amounts to 6 s (corresponding to a flow of 30 ml/min). If the lower limit value is not reached in this length of time, this can be due to an increased flow resistance in the container. In this case, the filling process can be aborted and/or a signal can be emitted to the user. This signal states that the container cannot be filled and that a new container must be used. An error memory entry can additionally take place. This can also apply accordingly to the case that the upper limit value is not reached.

It is thus conceivable that the error memory entries can read:

1. The minimum pressure, i.e. the upper limit value, was not reached
2. The lower switchover point, i.e. the lower limit value, was not reached It is furthermore conceivable that a plurality of timeouts are defined. A timeout (e.g. 30 s) can thus be defined for the first cycle which is longer than for all following cycles. The procedure takes into account that granulate or dry concentrate may still be present in the pipe line in the container through which the liquid is conveyed into the container and that this pipe line must first be flushed free.

It is thus conceivable that one or more timeouts or lengths of time are provided within which the lower limit value has to be reached. In this respect, the time window for the first cycle or cycles can be longer than for the following cycles.

Provision is made in a further embodiment of the invention that the first cycle or cycles of a filling process and/or the last cycle are not monitored for a reaching or exceeding or falling below of a limit value prior to an interruption of the filling process. This procedure takes account of the transient behavior of the system at the start of the filling process and after an interruption of the filling process.

It is also conceivable that the last cycle is not monitored on the interruption of the filling process. The reason for this is that the compressor which introduces compressed air or another gas into the container during the filling process in an embodiment is switched off or its airflow is stopped by the closing of a valve on an interruption. The smaller flow to the container which results from this has the consequence that other pressure conditions are produced in the container which could possibly result in a false alarm. The abortion is communicated to the system. The variable is deleted again on a new start of the filling process.

As already stated above, it is conceivable that the container is vented toward the atmosphere during the filling process. Nevertheless, characteristic pressure developments or pressure values result due to the pressure losses in the line system or hose system from the chamber to the container which can be measured and evaluated.

As was likewise stated above, provision is preferably made that the limit value is oriented on the maximum pressure measured up to that time within the framework of a filling process of a container, with preferably no reduction in the limit value taking place if the maximum pressures fall over time. A resetting of the limit values is preferably only provided and possible when it was confirmed or recognized at the machine side that a new container was placed onto the dialyzer.

The container content can be any desired solid which is soluble in the liquid, for example a powder, a granulate or also a liquid or a solid/liquid mixture. The use of an empty container or of a container only filled with air is also conceivable. It is preferably a dry acid concentrate, i.e. a concentrate which has a pH in the acidic range after the dissolving into water. A base concentrate, i.e. a concentrate which has a pH in the base range after the dissolving into water, is also covered by the invention.

It is pointed out at this point that the term "dry concentrate" can include the case that only solids are located in the container and no liquid, but also the case that liquid components are already present such as an acid, etc.

To achieve a sufficient mixing and thus an acceleration of the dissolving/mixing process, provision can be made that a gas, preferably air, is introduced into the container during or offset in time with respect to the filling of the container with liquid. For this purpose, the compressor already known above can be provided which introduces air into the container. The air can be introduced into the container via the same hose piece or via the same line as the liquid introduced by means of the balance chamber system.

Provision is made in a further embodiment of the invention that a new cycle is only initiated once a lower limit value for the pressure has been reached if a specific minimum length of time has elapsed since the cycle start. It is conceivable that the maximum filling flow is limited to e.g. a value of 700 ml/min. If the switchover pressure, i.e. the pressure on whose reaching a new cycle is initiated, is reached earlier, the balance chamber is only switched over in this case when the corresponding time for the flow limitation has also elapsed.

To avoid water deficiency alarms in weak RO (reverse osmosis) systems, the maximum filling flow is coupled to the water inflow.

The present invention furthermore relates to a dialyzer having means for filling a container, preferably containing at least one concentrate, with the concentrate being formed such that it forms at least one liquid concentrate or a part of a liquid concentrate on its solution in or its mixing with a liquid, preferably water, said liquid concentrate or part of a liquid concentrate being suitable for preparing at least one dialysis solution, and with the means for filling the container comprising at least one balance chamber system of the dialyzer which has chambers from which the liquid is moved into the container in the form of repeated cycles, with the dialyzer having at least one control or regulation unit which is configured and in particular programmed to carry out the method as described herein.

The dialyzer is thus suitable and intended to carry out the method in accordance with the invention. A control or regulation unit which carries out or initiates the method steps in accordance with the present invention serves this purpose.

The dialyzer can thus have an alarm transmitter and/or valves which emit(s) e.g. an optical and/or acoustic signal to the user in the event of the upper pressure limit value not being reached and/or which close(s) the valves or suppress(es) the activity of the balance chamber system so that the filling process of the container is stopped.

The dialyzer preferably has means which are configured such that one or more or all of the method steps in accordance with the invention can be carried out by these means.

BRIEF DESCRIPTION OF THE DRAWINGS

Further details and advantages of the invention will be explained in more detail with reference to an embodiment shown in the drawing. There are shown.

DETAILED DESCRIPTION OF THE PREFERRED EMBODIMENTS

Further scope of applicability of the present invention will become apparent from the detailed description given hereinafter, However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
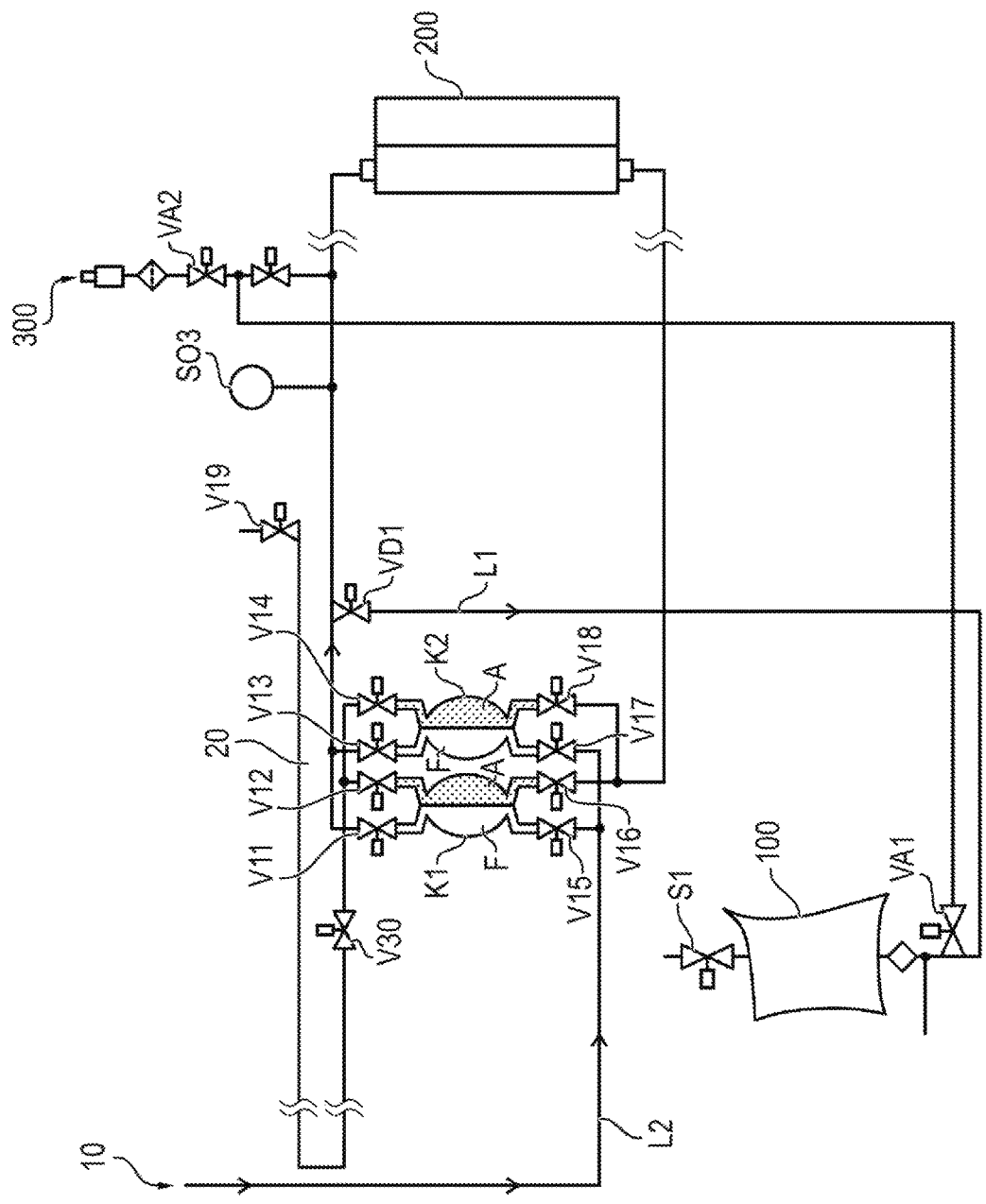
FIG. 1: a schematic flow diagram of a dialyzer in accordance with the invention.

A flow diagram of a dialyzer in accordance with the invention is shown in FIG. 1. Reference numeral 10 marks an RO water inflow from which the water flows to the balance chamber system 20.

The balance chamber system 20 comprises two chambers K1 and K2 which are connected in parallel, which both have rigid outer walls and in which a respective movable membrane extends which divides the chambers K1 and K2 into two respective regions, namely into a fresh water compartment F and into a used water compartment A.

To be able to use the balance chamber system 20 for filling the dry concentrate container 100, the liquid volume present in the used water part A of the balance chambers after the filling of the hose system is enclosed as a fixed oscillating volume by the closing of the valves V16 and V18 in the feed lines of both balance chambers K1 and K2. The oscillating volume thus comprises the volumes of the used water compartments A as well as of the line extending between them and having the valves V12 and V14 arranged therein. The oscillating volume is closed by the closed valves V16 and V18 as well as V30.

The term "used water part" is to be understood as the part A of the chambers which are acted on by consumed dialysis solution from the dialysis machine 200 during the treatment as well as the line piece connecting these chambers. The oscillating volume in the chambers is shown as dark in FIG. 1. The oscillating volume is pushed to and fro between the compartments A of chambers K1 and K2 connected by a line within the framework of the container filling.

The valves V12 and V14 in the outlet lines of chambers K1 and K2 are open so that the oscillating volume can be moved to and fro between the used water parts of the chambers K1 and K2. To close the oscillating volume to the outside, the outflow lines are shut off by closing the lines V30 and V19.

The filling of the container 100 takes place via the fresh water parts F of the chambers K1 and K2, i.e. via the parts of the chambers through which fresh dialysis solution is moved from a source to the dialysis machine 200 during a dialysis treatment. The fresh water parts of the chambers K1 and K2 are alternately filled and emptied. They are shown as light in FIG. 1.

The feed line of chamber K1 is opened in a phase by opening the valve V15 and its outflow line closed by means of the valve V11. At the same time, the valve V17 in the feed line of chamber K2 is closed and its outflow line is opened by opening the valve V13 so that water is conveyed from this fresh water part of chamber K2 via the open valve VD1 through the line L1 into the container 100. The oscillating volume flows into the used water part of chamber K2 for this purpose. At the same time, the fresh water part of chamber K1 is filled with water through the line L2.

In a new cycle, i.e. on a balance chamber switchover, the valve V17 is opened, the valve V13 is closed, the valve V15 is closed and the valve V11 is opened. The oscillating volume flows into the used water part of the chamber K1 so that the water located in its fresh water part is conveyed through the open valve VD1 and through the line L1 to the container 100, while the fresh water part of chamber K2 is simultaneously filled with water through the line L2.

The arrows in FIG. 1 symbolize the direction of flow.

The oscillating volume corresponds to the volume of a balance chamber K1 or K2 which have an identical volume.

The oscillating volume defines the filling volume for the dry concentrate container 100 conveyed per balance chamber switchover or per cycle. The total filling volume which is supplied to the container 100 in total is defined via the number of switchovers.

The dry concentrate container 100 is connected to the atmosphere via the open valve S1. A specific pressure development over time, such as pressure pulses, nevertheless arises during the filling of the container 100 with water from the balance chamber system 20 due to the flow resistance of the lines L1 or hoses through which the water flows from the balance chamber system 20 to the container 100. The level of these pressure pulses, i.e. the respective measured maximum pressure, is dependent on the conveyed liquid quantity and on the geometry of the fluid system. Since the absolute value of the pressure pulse is thus also dependent on the geometry and on the compliance of the fluid system, the level of the pressure pulse is preferably measured continuously for each system, i.e. also for each new container, in the method in accordance with the invention.

In order not to influence the measurement results, care should be taken that the flow resistance between the balance chamber system 20 and the container 100 is not varied during the filling process of a container 100, i.e. hose lengths, pipe diameters in the container, etc. should remain constant.

A pressure sensor S03, which, as can be seen from FIG. 1, is connected via a line to the line L1 which connects the balance chamber system 20 to the container 100, serves the pressure measurement in the embodiment described here.

The container 100 can be a bag or also a rigid container 100. One or more lines through which the liquid for dissolving the solid and, optionally, air for swirling and enhancing the dissolving process is introduced can project into the container.

Reference numeral 300 marks the line from a compressor which introduces air into the container 100. The valves VA2 and VA1 are open for this purpose. If the filling process is interrupted, these valves are closed.

Figure 2:
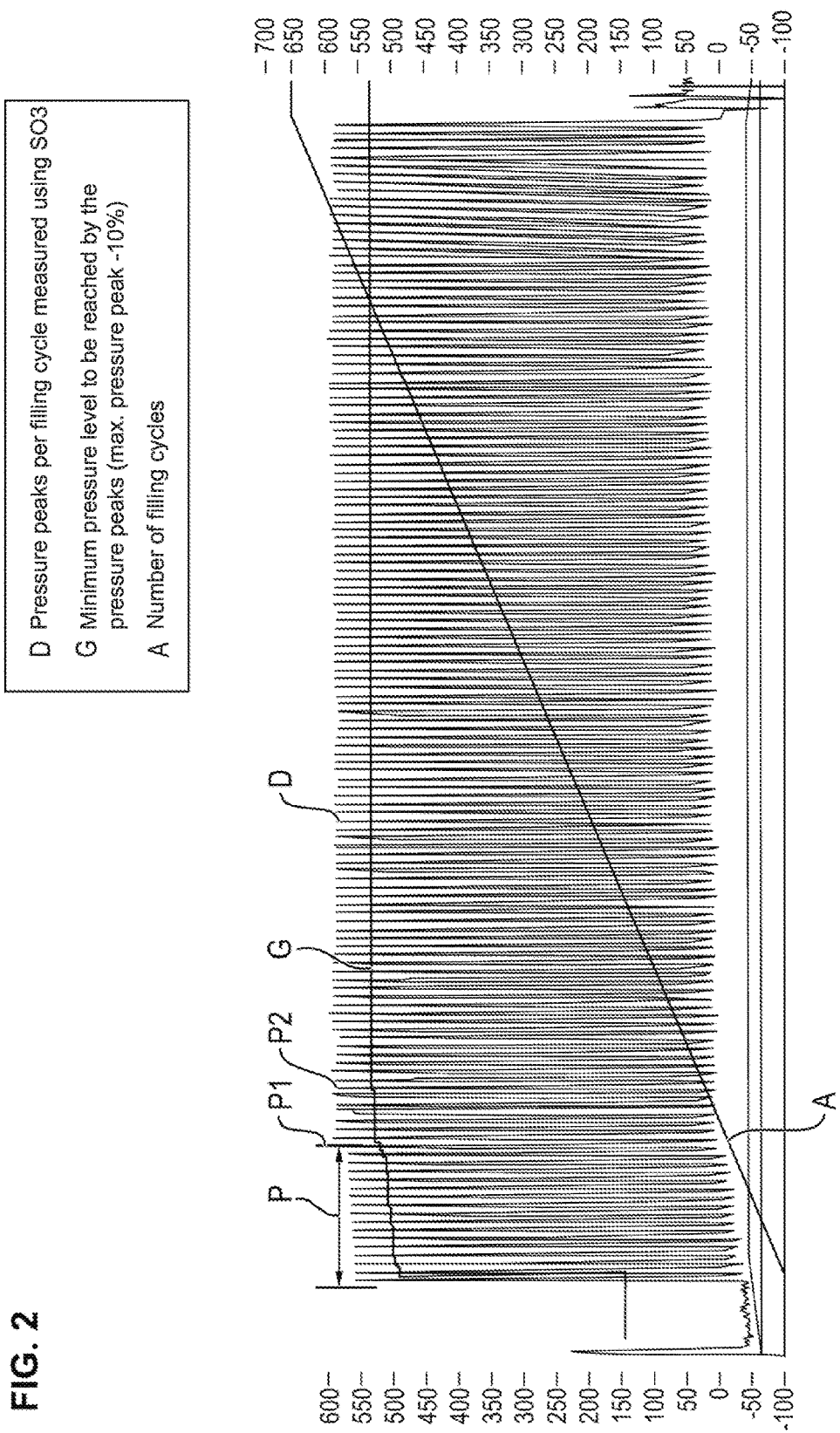
FIG. 2: the time development of the pressure, of the upper limit value and of the number of filling cycles during the filling of the container in a leak-free case.

The pressure peaks resulting on the emptying of the fresh water part and thus on the filling of the container 100 are shown in FIG. 2. As can be seen from FIG. 2, the pressure development comprises repeating peaks of which each represents the pressure development during a balance chamber cycle, i.e. during the movement of a liquid volume from a fresh water part of the chambers K1/K2 to the container 100. The peaks each have a maximum value and a smallest value.

The upper pressure value serves to recognize whether the balance chamber actually supplies liquid. It is recognized by the lower pressure value that the balance chamber was completely expressed.

The pressure peaks move at a plateau P until the container, which is preferably configured as a bag, is pressurized at the start of the filling process. There is subsequently a slight increase in the pressure peaks as can be seen from FIG. 2.

A pressure value of 10% less than the pressure peak reached up this point in time up to this cycle is used as a limit value for the pressure at least to be reached in each cycle. I.e. the largest pressure peak of a cycle reached up to that time forms the basis for the limit value which has to be reached in the following cycles. The respectively current limit value is marked by the reference symbol G in FIG. 2.

As can be seen from FIG. 2, the maximum pressure of the peaks increases in the plateau phase P so that the limit value G also increases. A further increase of the limit value G results at peak P1 and at peak P2 which have the highest pressure values up their occurrence. The limit value remains constant after peak P2 since no higher pressures have resulted after this peak P2.

The curve A shows the number of filling cycles for filling the container 100.

As can be seen from FIG. 2, the maximum pressure is above the limit value G at each peak in the embodiment shown so that neither an alarm signal is emitted nor an aborting of the filling process takes place.

Figure 3:
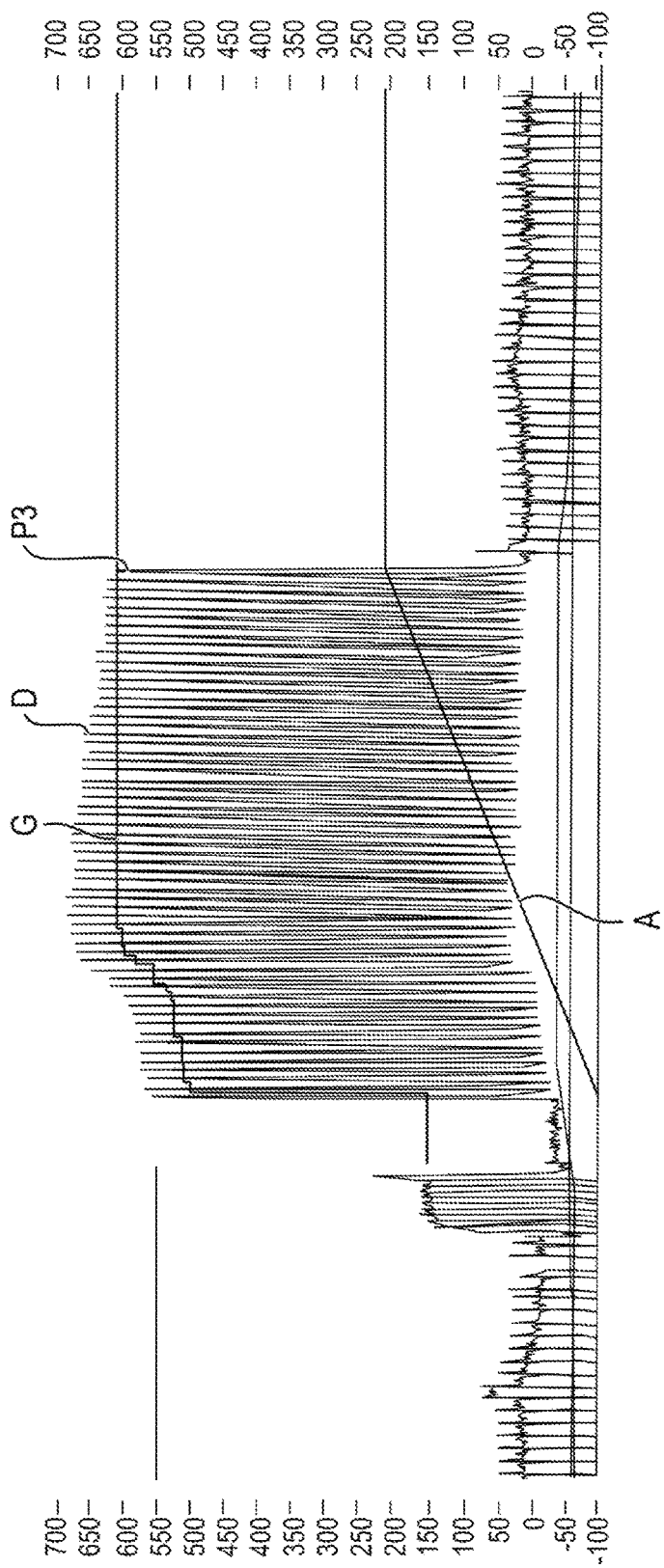
FIG. 3: the time development of the pressure, of the upper limit value and of the number of filling cycles during the filling of the container on the occurrence of a leak.

FIG. 3 shows another development of the pressure, of the limit value as well as the number of cycles carried out. In the example in accordance with FIG. 3, the maximum pressure value of the peak P3 does not exceed the limit value G current at this time, which has the consequence that the filling process is aborted and an indication signal is emitted to the user.

The non-reaching of the limit value G in the example in accordance with FIG. 3 is considered due to the fact that the oscillating volume reduces due to a leak in the system such as a leak in the valves closing the oscillating volume, whereby the filling volume directly coupled thereto also reduces. If the maximum pressure falls below the limit value, the conclusion is drawn that the filling volume conveyed per balance chamber switchover has fallen below a limit value. An alarm is triggered and/or the filling process is stopped.

Leak rates of ≥50 µl/switchover can be detected using the procedure in accordance with the invention. As stated above, this value and the above-named values are examples which do not limit the invention.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of filling a container that contains a concentrate, with the concentrate being provided so as to form a liquid concentrate or a part of a liquid concentrate on solution of the concentrate in, or dilution of the concentrate with, a liquid, the liquid concentrate or the part of a liquid concentrate being suitable for preparing a dialysis solution, and with the filling of the container taking place via a balance chamber system of a dialyzer which has a plurality of chambers from which the liquid is conveyed into the container in a form of repeating cycles, said method comprising:

prior to a blood treatment with the dialyzer, measuring a time development of the pressure of the liquid being conveyed from one of the plurality of chambers into the container during a cycle of the filling of the container, the time development of the pressure of the liquid corresponding to a magnitude of pressure pulses generated during an expulsion phase of the liquid; and at least one of emitting an alarm signal, and stopping the filling of the container, if a measured maximum pressure in a cycle does not reach or does not exceed a limit value.

2. The method in accordance with claim 1, wherein the balance chamber system of the dialyzer has at least two chambers, and an oscillating volume flows to and fro between the at least two chambers.

3. The method in accordance with claim 1, wherein the limit value depends on a maximum value which was measured or which is predefined in a preceding cycle.

4. The method in accordance with claim 3, wherein the limit value lies below a highest maximum pressure measured in the preceding cycle by a specific percentage or by a specific absolute value.

5. The method in accordance with claim 1, wherein the limit value is not lowered during the filling.

6. The method in accordance with claim 1, wherein the pressure of the liquid being conveyed is measured in a line between one of the plurality of chambers and the container, or in a line in communication with the line between the one of the plurality of chambers and the container.

7. The method in accordance with claim 1, wherein the pressure of the liquid being conveyed first rises on an emptying of one of the plurality of chambers and then drops, and at least one of the alarm signal is emitted, and the filling of the container is stopped, when a lower limit value for the pressure is not reached, or is not fallen below, within a specific time window since the cycle start.

8. The method in accordance with claim 7, wherein a specific time window for a first cycle or cycles is longer than for subsequent cycles.

9. The method in accordance with claim 1, wherein at least one of a first cycle or cycles of a filling, and a last cycle, is not monitored before the stopping of the filling.

10. The method in accordance with claim 1, wherein the container is vented to the atmosphere during the filling.

11. The method in accordance with claim 1, wherein the limit value is only reset upon a confirmation or a recognition that a new container has been placed onto the dialyzer.

12. The method in accordance with claim 1, wherein the concentrate located in the container is at least one of a liquid and a dry concentrate.

13. The method in accordance with claim 1, wherein a gas is introduced into the container during the filling of the container with the liquid.

14. The method in accordance with claim 1, wherein a new cycle is only initiated once a lower limit for the pressure of the liquid being conveyed has been reached if a specific minimum length of time has elapsed since the cycle start.

15. The method according to claim 1, wherein the liquid is water.

16. The method according to claim 2, wherein the oscillating volume corresponds to a volume of one of the at least two chambers.

17. The method according to claim 5, wherein the limit value is not lowered if the measured maximum pressure is smaller in one cycle than in a previous cycle.

18. The method according to claim 12, wherein the dry concentrate is a dry acid concentrate.

19. The method according to claim 13, wherein the gas is air.

* * * * *